(12) United States Patent
Katakura

(10) Patent No.: US 8,684,915 B2
(45) Date of Patent: Apr. 1, 2014

(54) ENDOSCOPE OPTICAL SYSTEM

(75) Inventor: Masahiro Katakura, Chofu (JP)

(73) Assignee: Olympus Medical Systems Corp., Tokyo (JP)

(*) Notice: Subject to any disclaimer, the term of this patent is extended or adjusted under 35 U.S.C. 154(b) by 38 days.

(21) Appl. No.: 13/591,794

(22) Filed: Aug. 22, 2012

(65) Prior Publication Data
US 2013/0044361 A1 Feb. 21, 2013

Related U.S. Application Data

(63) Continuation of application No. PCT/JP2011/076380, filed on Nov. 16, 2011.

(30) Foreign Application Priority Data

Dec. 15, 2010 (JP) .................................. 2010-279786

(51) Int. Cl.
*A61B 1/06* (2006.01)

(52) U.S. Cl.
USPC .......................... 600/160; 359/226.1; 359/831

(58) Field of Classification Search
USPC ................. 128/6; 362/572; 359/196.1–226.3,
359/831–836; 606/46, 170; 600/101–183,
600/191, 200, 224, 249
See application file for complete search history.

(56) References Cited

U.S. PATENT DOCUMENTS

| | | | |
|---|---|---|---|
| 4,042,295 A | 8/1977 | Yamasita et al. | |
| 6,638,216 B1 | 10/2003 | Durell | |
| 7,221,522 B2 | 5/2007 | Tesar et al. | |
| 7,405,887 B2 | 7/2008 | Iwasawa | |
| 2006/0252995 A1 | 11/2006 | Hoeg et al. | |
| 2006/0256450 A1 | 11/2006 | Tesar et al. | |
| 2012/0035422 A1* | 2/2012 | Lei et al. ...................... 600/173 |

FOREIGN PATENT DOCUMENTS

| | | |
|---|---|---|
| JP | 51-044937 | 4/1976 |
| JP | 2005-266175 | 9/2005 |
| JP | 2006-201796 | 8/2006 |
| JP | 2006-204924 | 8/2006 |
| JP | 2010-128034 | 6/2010 |
| JP | 4503535 | 7/2010 |

OTHER PUBLICATIONS

International Search Report, issued in corresponding International Patent Application No. PCT/JP2011/076380.* (2012).

* cited by examiner

*Primary Examiner* — Jennifer L. Doak
(74) *Attorney, Agent, or Firm* — Kenyon & Kenyon LLP

(57) ABSTRACT

An endoscope optical system includes a negative lens that focuses light entering along an incident optical axis, a first prism that deflects and emits the light from the negative lens along a first axis substantially orthogonal to the incident optical axis, a second prism having a first reflecting surface, which deflects the light from the first prism along a second axis substantially orthogonal to the first axis, and a second reflecting surface that deflects and emits the light substantially parallel to the first axis and that faces the first prism, a third prism that deflects the light from the second prism substantially parallel to the incident optical axis, and a positive lens that focuses the light from the second prism, in this order from an object side, the negative lens and the first prism being rotatable about the first axis relative to the second prism.

5 Claims, 6 Drawing Sheets

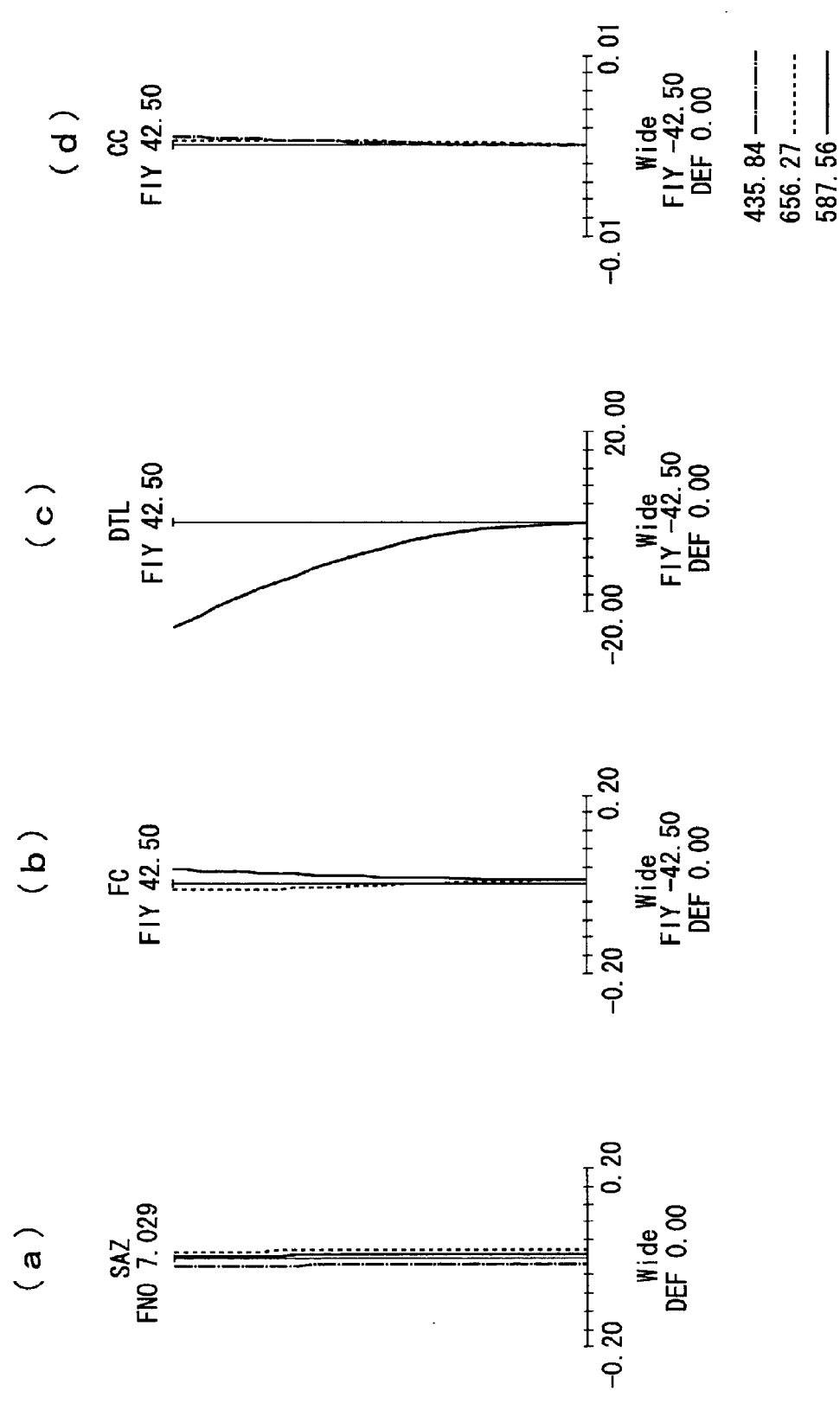

ENDOSCOPE OPTICAL SYSTEM

CROSS-REFERENCE TO RELATED APPLICATIONS

This is a continuation of International Application PCT/JP2011/076380, with an international filing date of Nov. 16, 2011, which is hereby incorporated by reference herein in its entirety. This application is based on Japanese Patent Application No. 2010-279786, the contents of which are incorporated herein by reference.

TECHNICAL FIELD

The present invention relates to an endoscope optical system.

BACKGROUND

In known endoscopes in the related art, the direction of the field of view of an endoscope is made adjustable by changing the direction of the distal end surface of the endoscope by swiveling or rotating a mirror or prism arranged at the distal end portion thereof (for example, see PTLs (Patent Literatures) 1 and 2).

CITATION LIST

Patent Literature

{PTL 1} U.S. Pat. No. 6,638,216.
{PTL 2} Japanese Unexamined Patent Application, Publication No. 2006-201796.
{PTL 3} Publication of Japanese Patent No. 4503535.

SUMMARY OF INVENTION

The present invention is to provide an endoscope optical system that is capable of obtaining an endoscope-image with high image quality while keeping the diameter of a distal end portion of the endoscope small even if the direction of the field of view of the endoscope is made adjustable.

Solution to Problem

The present invention provides the following solutions.

A first aspect of the present invention is an endoscope optical system including a negative lens that focuses light entering along an incident optical axis, a first prism that deflects and emits the light that has been focused by the negative lens in a direction along a first axis substantially orthogonal to the incident optical axis, a second prism that has a first reflecting surface, which deflects the light emitted from the first prism in a direction of a second axis substantially orthogonal to the first axis, and a second reflecting surface that deflects and emits the light, which has been deflected in the direction of the second axis, in a returning direction substantially parallel to the first axis, and that is disposed so as to face the first prism, a third prism that deflects the light, which has been emitted from the second prism, in a direction substantially parallel to the incident optical axis, and a positive lens that focuses the light emitted from the third prism, in this order from an object side, wherein the negative lens and the first prism are provided so as to be rotatable about the first axis relative to the second prism, and wherein refractive indices of the first prism, the second prism, and the third prism satisfy the following conditional expression $$1.7 < (Np1 + Np2 + Np3)/3 < 2.4 \qquad (3)$$

where $Np1$ is a d-line refractive index of the first prism, $Np2$ is a d-line refractive index of the second prism, and $Np3$ is a d-line refractive index of the third prism.

A second aspect of the present invention is an endoscope optical system including a negative lens that focuses light entering along an incident optical axis, a first prism that deflects and emits the light that has been focused by the negative lens in a direction along a first axis substantially orthogonal to the incident optical axis, a second prism that has a first reflecting surface, which deflects the light emitted from the first prism in a direction of a second axis substantially orthogonal to the first axis, and that is disposed so as to face the first prism, and a positive lens that focuses the light emitted from the second prism, in this order from an object side, wherein the negative lens and the first prism are provided so as to be rotatable about the first axis relative to the second prism, and wherein refractive indices of the first prism and the second prism satisfy the following conditional expression $$2.0 < (Np1 + Np2)/2 < 2.4 \qquad (1)$$

where $Np1$ is a d-line refractive index of the first prism, and $Np2$ is a d-line refractive index of the second prism.

BRIEF DESCRIPTION OF DRAWINGS

FIG. 6 is an aberration diagram of the lenses in the example in FIG. 5.

DESCRIPTION OF EMBODIMENTS

An endoscope optical system 1 according to a first embodiment of the present invention will be described below with reference to the drawings.

Figure 1:
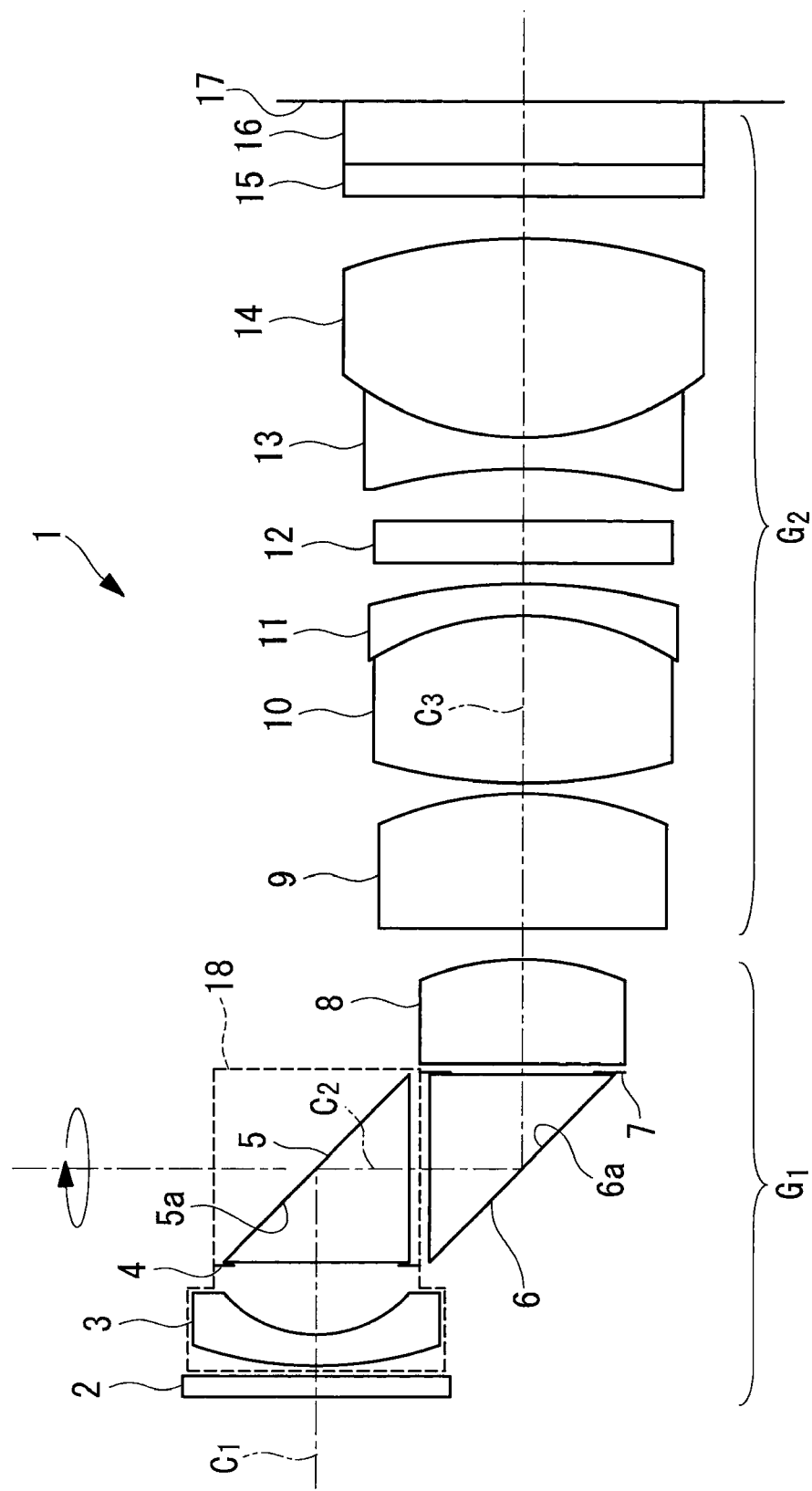
FIG. 1 is an overall configuration diagram showing an endoscope optical system according to a first embodiment of the present invention.

As shown in FIG. 1, an endoscope optical system 1 according to this embodiment is provided in a distal end of an insertion portion of a rigid endoscope and is provided with a front group G1 and a rear group G2.

The front group G1 is provided with a cover glass (first optical member) 2, a negative lens 3, a flare stop 4, a first prism 5, a second prism 6, an aperture stop 7, and a positive lens 8, in this order from the object side. The rear group G2 is provided with a plurality of lenses 9 to 15 including at least one positive lens and at least one negative lens that focus the light emerging from the front group G1 and a flat glass plate (second optical member) 16 that is disposed so as to face an image-acquisition surface 17 of an image-acquisition device.

The negative lens 3 focuses the light entering along an incident optical axis C1 from the object.

The flare stop 4 stops down the light focused by the negative lens 3 to define the F-number of the entire endoscope optical system 1.

The first prism 5 is a triangular prism that emits the light coming from the object side that has been focused by the negative lens 3 by deflecting the light by an angle of substantially 90° at a reflecting surface 5a in the direction along a first axis C2 that is substantially orthogonal to the incident optical axis C1.

In addition, the second prism 6 is also a triangular prism that emits the light that has been emitted from the first prism 5 in the direction along the first axis C2 by deflecting the light by an angle of substantially 90° at a reflecting surface (first reflecting surface) 6a in the direction along a second axis C3 that is substantially parallel to the incident optical axis C1.

The positive lens 8 focuses the light that has been emitted from the second prism 6 in the direction along the second axis C3, and emits the focused light towards the rear group G2.

The refractive indices of the first prism 5 and second prism 6 satisfy the following conditional expression (1).

$$1.7<(Np1+Np2A)/2<2.4 \quad (1)$$

Here, Np1 is the d-line refractive index of the first prism 5 and Np2A(Np2) is the d-line refractive index of the second prism 6.

It is preferred that $1.8<(Np1+Np2A)/2<2.3$ be satisfied, and it is more preferred that $2.0<(Np1+Np2A)/2<2.2$ be satisfied.

In addition, in this embodiment, the length along the optical axes C1 and C2 in the first prism 5 and the length along the optical axes C2 and C3 in the second prism 6 satisfy the following conditional expression (2).

$$0.8<DP1/DP2A<1.2 \quad (2)$$

Here, DP1 is the length along the optical axes C1 and C2 in the first prism 5, and DP2A (DP2) is the length along the optical axes C2 and C3 in the second prism 6.

In addition, the negative lens 3, the flare stop 4, and the first prism 5 are integrated in a casing 18 and are provided so as to be rotatable about the first axis C2 relative to the cover glass 2, the second prism 6, the positive lens 8, and the rear group G2.

In addition, in this embodiment, the following conditional expression (6) is satisfied, where enp is the distance to an entrance pupil position, which is an image position of the stop when viewed from the object side, and fl is the focal distance of the entire endoscope optical system 1 from the cover glass 2 to the flat glass plate 16.

$$0.1<enp/fl<5 \quad (6)$$

It is preferred that $0.3<enp/fl<2$ be satisfied, and it is more preferred that $0.6<enp/fl<1$ be satisfied.

The operation of the thus-configured endoscope optical system 1 according to this embodiment will be described below.

With the endoscope optical system 1 according to this embodiment, the direction of the field of view of the endoscope can be changed by swiveling the incident optical axis C1 relative to the second axis C3 that is the optical axis of the rear group G2 by rotating the negative lens 3, the flare stop 4, and the first prism 5 about the first axis C2.

In this case, it is possible to dispose the optical axis of the positive lens 8 in the direction along the second axis C3, which is substantially parallel to the plane including the incident optical axis C1, by deflecting the light that has been focused by the negative lens 3 by an angle of 90° twice by the two triangular prisms 5 and 6, and therefore, it is possible to arrange the plurality of lenses 9 to 16 constituting the rear group G2 along the longitudinal direction of the insertion portion of the endoscope. As a result, the size of the image-acquisition device, which is arranged so as to face the flat glass plate 16 disposed at the rearmost stage of the rear group G2, can be determined by the diameter of the insertion portion, and if a sufficiently large diameter can be secured, it is possible to employ a large image-acquisition device to achieve improved image quality.

In addition, according to the endoscope optical system 1 of this embodiment, by satisfying conditional expression (1), the refractive indices of the two prisms 5 and 6 disposed between the negative lens 3 and the positive lens 8 are set high, thereby reducing the air-equivalent length of the optical path in the prisms 5 and 6. By doing so, there is an advantage in that, by reducing the apparent distance between the negative lens 3 and the positive lens 8, an increase in the image height can be suppressed and the occurrence of aberrations can be prevented, regardless of the presence of the prisms 5 and 6 for changing the direction of the field of view. In other words, there are advantages in that, because a separate positive lens for preventing an increase in image height need not be provided, it is possible to configure the optical system compactly, and at the same time, it is possible to suppress aberrations, thus obtaining a clear image.

In addition, by satisfying conditional expression (2), it is possible to minimize a gap formed between the prisms 5 and 6 and to shorten the air-equivalent length.

Furthermore, because the light that has entered the negative lens 3 along the incident optical axis C1 is deflected twice by the two prisms 5 and 6, there are advantages in that the image of the object entering the image-acquisition device need not be inverted, and an upright image can be observed with the obtained image directly rather than subjecting the obtained image information to inversion processing.

In addition, according to the endoscope optical system 1 of this embodiment, by satisfying conditional expression (6), the distance from the apex of the negative lens 3 to the entrance pupil position is set relatively short relative to the focal distance of the entire endoscope optical system 1, and therefore, it is possible to avoid an increase in the size of the rotationally driven negative lens 3 and to configure a movable portion compactly.

In addition, according to the endoscope optical system 1 of this embodiment, because the incident optical axis C1 and the second axis C3 are substantially parallel and separated from each other by a gap, there are advantages in that it is possible to suppress interference between a movable portion including the negative lens 3, the flare stop 4, and the first prism 5, which are rotated, and a stationary portion including the second prism 6, the aperture stop 7, and the positive lens 8, and it is possible to ensure a wide rotation angle range.

Next, an endoscope optical system 20 according to a second embodiment of the present invention will be described below with reference to the drawings.

In the description of this embodiment, parts having the same configuration as those in the endoscope optical system 1 according to the first embodiment described above will be assigned the same reference numerals, and a description thereof will be omitted.

Figure 2:
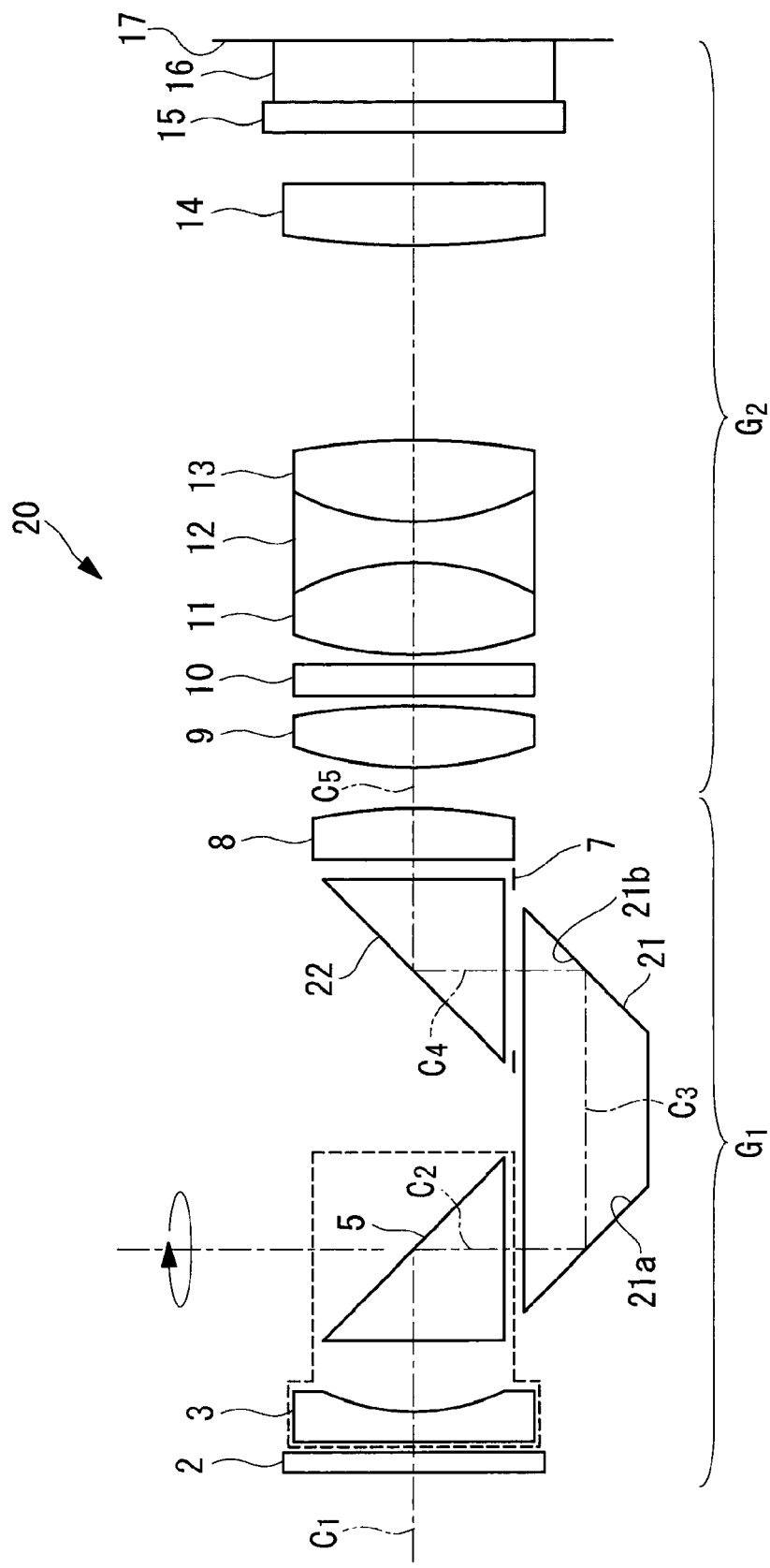
FIG. 2 is an overall configuration diagram showing an endoscope optical system according to a second embodiment of the present invention.

As shown in FIG. 2, the endoscope optical system 20 according to this embodiment differs from the endoscope optical system 1 according to the first embodiment in that a second prism 21 constituting the front group G1 is formed of a trapezoidal prism, and a third prism 22 formed of a triangular prism is provided.

In the embodiment, the second prism 21 formed of a trapezoidal prism deflects the light that has been deflected towards the first axis C2 by the first prism 5 by an angle of substantially 90° at a first reflecting surface 21a in the direction of the second axis C3, and thereafter, the light is deflected by an angle of substantially 90° at a second reflecting surface 21b and is emitted along a third axis C4, which is substantially parallel to the first axis C2, in a direction so as to approach the incident optical axis C1. In addition, the aperture stop 7 is disposed between the second prism 21 and the third prism 22.

The third prism 22 deflects the light that has been emitted from the second prism 21 by an angle of substantially 90°, thereby emitting the light in the direction along an optical axis C5 of the positive lens 8 that is disposed in substantially the same plane as that of the incident optical axis C1.

In this embodiment, the refractive indices of the first prism 5, the second prism 21, and the third prism 22 satisfy the following conditional expression (3).

$$1.7 < (Np1 + Np2B + Np3)/3 < 2.4 \quad (3)$$

Here, Np1 is the d-line refractive index of the first prism 5, Np2B(Np2) is the d-line refractive index of the second prism 21, and Np3 is the d-line refractive index of the third prism 22.

It is preferred that $1.8 < (Np1+Np2B+Np3)/3 < 2.3$ be satisfied, and it is more preferred that $2.0 < (Np1+Np2 B+Np3)/3 < 2.2$ be satisfied.

In addition, in this embodiment, the length along the optical axes C1 and C2 in the first prism 5 and the length along the optical axes C4 and C5 in the third prism 22 satisfy the following conditional expression (4).

$$0.8 < DP1/DP3 < 1.2 \quad (4)$$

Here, DP1 is the length along the optical axes C1 and C2 in the first prism 5, and DP3 is the length along the optical axes C4 and C5 in the third prism 22.

Furthermore, in this embodiment, the length along the optical axes C2, C3, and C4 in the second prism 21 and the length along the optical axes C4 and C5 in the third prism 22 satisfy the following conditional expression (5).

$$0.5 < DP2B/DP3 < 7 \quad (5)$$

Here, DP2B (DP2) is the length along the optical axes C2, C3, and C4 in the second prism 21.

It is preferred that $1 < DP2B/DP3 < 5$ be satisfied, and it is more preferred that $2 < DP2B/DP3 < 3$ be satisfied.

The operation of the thus-configured endoscope optical system 20 according to this embodiment will be described below.

With the endoscope optical system 20 according to this embodiment, the direction of the field of view of the endoscope can be changed by swiveling the incident optical axis C1 relative to the optical axis C5 of the rear group G2 by rotating the negative lens 3 and the first prism 5 about the first axis C2.

In this case, after the light that has been focused by the negative lens 3 is deflected by an angle of 90° by the first prism 5, which is formed of a triangular prism, the light is deflected twice by an angle of 90° at the first reflecting surface 21a and the second reflecting surface 21b of the second prism 21, which is formed of a trapezoidal prism, and is then deflected by an angle of 90° by the third prism 22, which is formed of a triangular prism; therefore, it is possible to dispose the optical axis C5 of the positive lens 8 on the plane including the incident optical axis C1. By doing so, it is possible to dispose the incident optical axis C1 of the front group G1 and the optical axis C5 of the rear group G2 coaxially, allowing them to be disposed in the insertion portion in the most efficient way.

In addition, as in the first embodiment, the plurality of lenses 9 to 16 constituting the rear group G2 can be arranged along the longitudinal direction of the insertion portion of the endoscope, the size of the image-acquisition device, which is arranged so as to face the flat glass plate 16 disposed at the rearmost stage of the rear group G2, can be determined by the diameter of the insertion portion, and if a sufficiently large diameter can be secured, it is possible to employ a large image-acquisition device to achieve improved image quality.

In addition, according to the endoscope optical system 20 of this embodiment, by satisfying conditional expression (3), the refractive indices of the three prisms 5, 21, and 22 disposed between the negative lens 3 and the positive lens 8 are set high, thereby reducing the air-equivalent length of the optical path in the prisms 5, 21, and 22. By doing so, there is an advantage in that, by reducing the apparent distance between the negative lens 3 and the positive lens 8, an increase in the image height can be suppressed and the occurrence of aberrations can be prevented, regardless of the presence of the prisms 5, 21, and 22 for changing the direction of the field of view. In other words, there are advantages in that, because a separate positive lens for preventing an increase in image height need not be provided, it is possible to configure the endoscope optical system 20 compactly, and at the same time, it is possible to suppress aberrations, thus obtaining a clear image.

In this way, an endoscope-image with high image quality can be obtained while keeping the diameter of a distal end portion of the endoscope optical system 20 small, even if the direction of the field of view of the endoscope optical system 20 is made adjustable.

Furthermore, because the light that has entered the negative lens 3 along the incident optical axis C1 is deflected four times by the three prisms 5, 21, and 22, there are advantages in that the image of the object entering the image-acquisition device need not be inverted, and an upright image can be observed with the obtained image directly without subjecting the obtained image information to inversion processing.

In addition, since the incident optical axis C1 and the optical axis of the positive lens 8 is disposed in substantially the same plane, it is possible to configure the endoscope optical system 20 compactly by efficiently utilizing a space between the prism 5, 21, and 22. By efficiently utilizing the space in the endoscope distal end portion, it is possible to make the endoscope optical system 20 smaller in the radial direction.

In addition, according to the endoscope optical system 20 of this embodiment, by satisfying conditional expression (4), it is possible to minimize the gap formed between the prisms 5 and 22 and to minimize the air-equivalent length.

In addition, in conditional expression (5), if DP2B/DP3 is 0.5 or less, the second prism 21 becomes too small relative to the third prism 22, causing the first prism 5 to interfere with the third prism 22, which then makes the rotation thereof difficult, and if DP2B/DP3 is 7 or more, the negative lens 3, which is rotated, becomes too large relative to the second prism 21. By satisfying conditional expression (5), it is possible to configure an optical system without the problems described above.

Example

Next, an example of the endoscope optical system 1 according to the first embodiment of the present invention will be described below with reference to the drawings.

Figure 3:
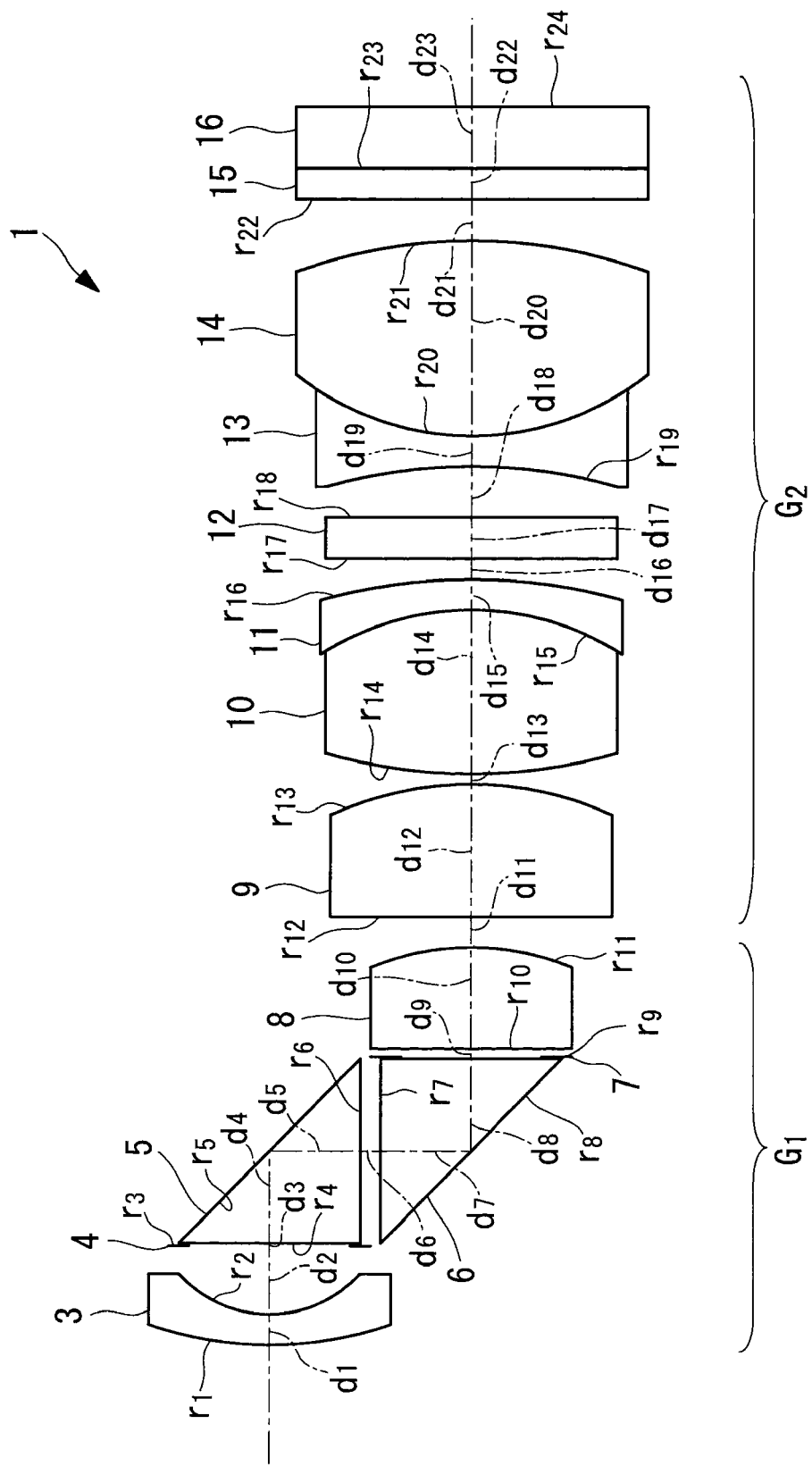
FIG. 3 is a lens layout diagram showing an example of the endoscope optical system according to the first embodiment of the present invention.

As shown in FIG. 3, the endoscope optical system 1 according to this example is provided with the front group G1 and the rear group G2.

The front group G1 is provided with the negative lens 3 formed of a meniscus lens, the flare stop 4, the two triangular prisms 5 and 6, the aperture stop 7, and the positive lens 8 formed of a plano-convex lens.

The rear group G2 is provided with a plano-convex lens 9, a combined lens formed of a biconvex lens 10 and a meniscus lens 11, a flat glass plate 12, a combined lens formed of a biconcave lens 13 and a biconvex lens 14, and the flat glass plate 16.

The lens data for these lenses is shown below.

| Surface number | R | D | Nd | Vd |
|---|---|---|---|---|
| 1 | 6.675 | 0.40 | 2.00330 | 28.27 |
| 2 | 1.392 | 0.65 | | |
| 3 | ∞ (flare stop) | 0.05 | | |
| 4 | ∞ | 1.00 | 2.00330 | 28.27 |
| 5 | ∞ (reflecting surface) | 1.00 | 2.00330 | 28.27 |
| 6 | ∞ | 0.20 | | |
| 7 | ∞ | 1.00 | 2.00330 | 28.27 |
| 8 | ∞ (reflecting surface) | 1.00 | 2.00330 | 28.27 |
| 9 | stop | 0.10 | | |
| 10 | ∞ | 1.00 | 1.67300 | 38.15 |
| 11 | −3.567 | 0.50 | | |
| 12 | ∞ | 1.36 | 1.49700 | 81.60 |
| 13 | −4.385 | 0.10 | | |
| 14 | 6.516 | 1.77 | 1.58913 | 61.14 |
| 15 | −2.719 | 0.50 | 1.88300 | 40.76 |
| 16 | −6.888 | 0.30 | | |
| 17 | ∞ | 0.60 | 1.51800 | 74.60 |
| 18 | ∞ | 0.63 | | |
| 19 | −5.250 | 0.50 | 1.84666 | 23.78 |
| 20 | 2.774 | 2.50 | 1.72916 | 54.68 |
| 21 | −3.992 | 0.53 | | |
| 22 | ∞ | 0.40 | 1.51633 | 64.14 |
| 23 | ∞ | 1.00 | 1.61350 | 50.20 |
| 24 | ∞ | | | |

In addition, in this example, $(Np1+Np2A)/2=2.01$, $DP1/DP2A=2.00/2.00=1.00$, and $enp/fl=0.67$, and conditional expressions (1), (2), and (6) are satisfied.

Figure 4:
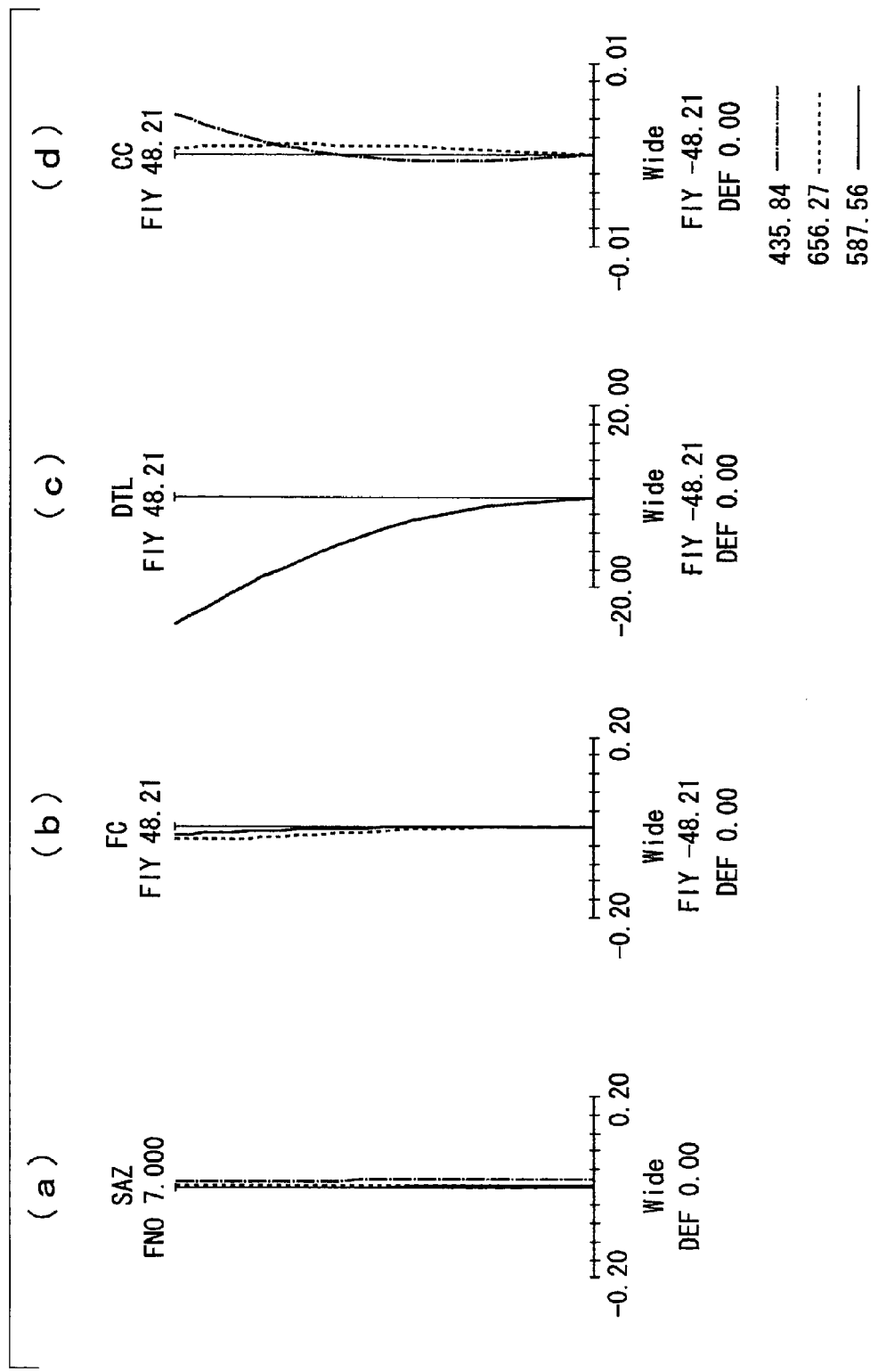
FIG. 4 is an aberration diagram of the lenses in the example in FIG. 3.

Aberration diagrams of spherical aberration (SAZ), astigmatism (FC), distortion (DTL), and lateral chromatic aberration (CC) are shown in (a), (b), (c), and (d) in FIG. 4, respectively. By using a plurality of lens types in Example 1, it is possible to provide an optical system whose aberrations are sufficiently corrected to allow it to be applied to an endoscope.

Next, an example of the endoscope optical system 20 according to the second embodiment of the present invention will be described below with reference to the drawings.

Figure 5:
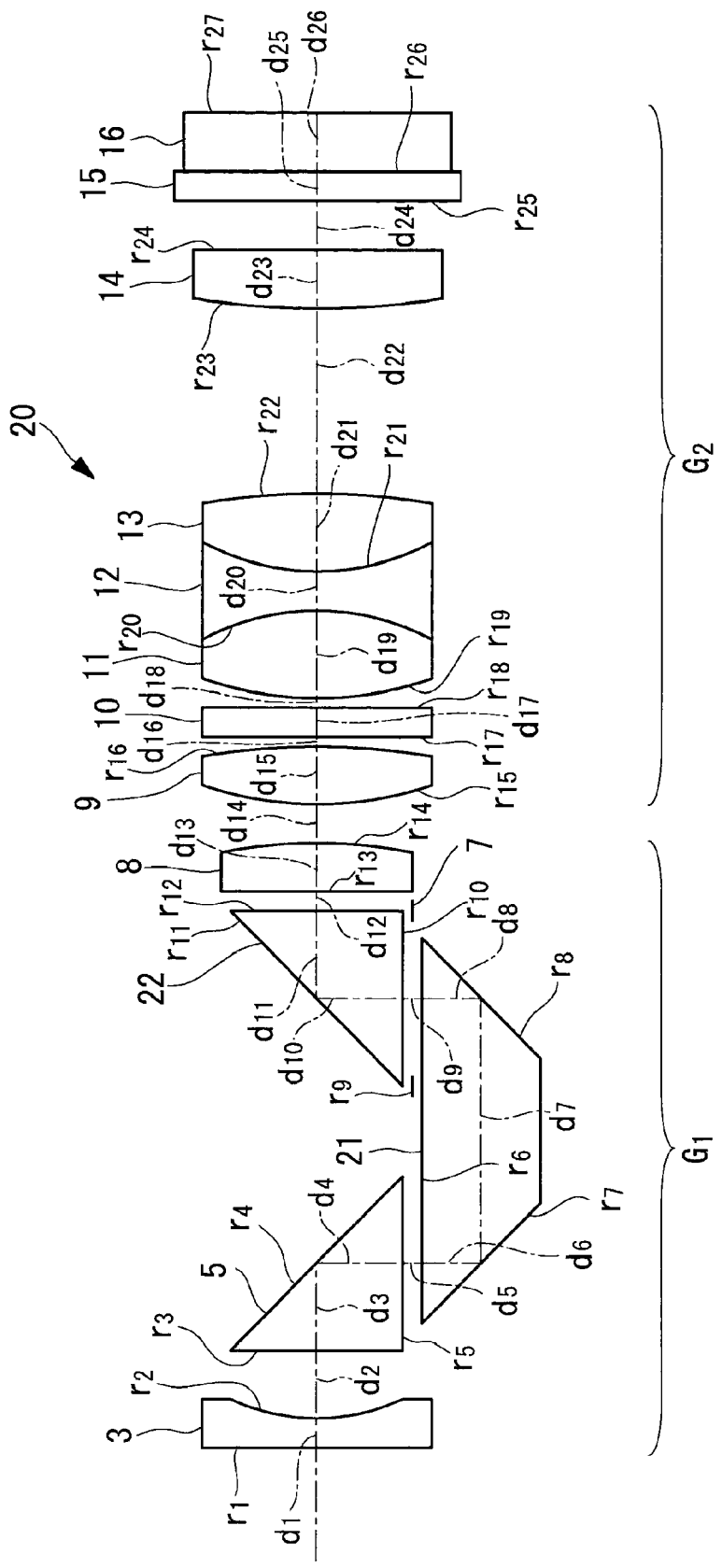
FIG. 5 is a lens layout diagram showing an example of the endoscope optical system according to the second embodiment of the present invention.

As shown in FIG. 5, the endoscope optical system 20 according to this example is provided with the front group G1 and the rear group G2.

The front group G1 is provided with the negative lens 3 formed of a meniscus lens, the triangular prism 5, the trapezoidal prism 21, the aperture stop 7, the triangular prism 22, and the positive lens 8 formed of a plano-convex lens.

The rear group G2 is provided with the biconvex lens 9; the flat glass plate 10; a combined lens formed of the biconvex lens 11, the meniscus lens 12, and the biconvex lens 13; the plano-convex lens 14; and the flat glass plate 16.

The lens data for these lenses is shown below.

| Surface number | R | D | Nd | Vd |
|---|---|---|---|---|
| 1 | ∞ | 0.40 | 2.00330 | 28.27 |
| 2 | 2.500 | 1.00 | | |
| 3 | ∞ | 1.40 | 2.00330 | 28.27 |
| 4 | ∞ (reflecting surface) | 1.40 | 2.00330 | 28.27 |
| 5 | ∞ | 0.10 | | |
| 6 | ∞ | 1.00 | 2.00330 | 28.27 |
| 7 | ∞ (reflecting surface) | 4.50 | 2.00330 | 28.27 |
| 8 | ∞ (reflecting surface) | 1.00 | 2.00330 | 28.27 |
| 9 | stop | 0.30 | | |
| 10 | ∞ | 1.20 | 2.00330 | 28.27 |
| 11 | ∞ (reflecting surface) | 1.20 | 2.00330 | 28.27 |
| 12 | ∞ | 0.30 | | |
| 13 | ∞ | 0.80 | 1.84666 | 23.78 |
| 14 | −8.682 | 0.70 | | |
| 15 | 3.654 | 1.10 | 1.49700 | 81.54 |
| 16 | −15.821 | 0.20 | | |
| 17 | ∞ | 0.60 | 1.51800 | 74.60 |
| 18 | ∞ | 0.20 | | |
| 19 | 5.496 | 1.40 | 1.49700 | 81.54 |
| 20 | −3.254 | 0.70 | 2.00330 | 28.27 |
| 21 | 3.254 | 1.25 | 1.58144 | 40.75 |
| 22 | −40.944 | 2.19 | | |
| 23 | 11.201 | 1.00 | 1.49700 | 81.54 |
| 24 | ∞ | 0.70 | | |
| 25 | ∞ | 0.50 | 1.51633 | 64.14 |
| 26 | ∞ | | 1.61350 | 50.20 |
| 27 | ∞ | | | |

In addition, in this example, $(Np1+Np2A)/2=2.01$, $(Np1+Np2B+Np3)/3=2.01$, $DP1/DP3=2.80/2.40=1.17$, $DP2B/DP3=6.50/2.40=2.71$, and $enp/fl=0.83$, and conditional expressions (1) and (3) to (6) are satisfied.

Aberration diagrams of spherical aberration (SAZ), astigmatism (FC), distortion (DTL), and lateral chromatic aberration (CC) are shown in (a), (b), (c), and (d) in FIG. 6, respectively. By using a plurality of lens types in Example 2, it is possible to provide an optical system whose aberrations are sufficiently corrected to allow it to be applied to an endoscope.

| {Reference Signs List} | |
|---|---|
| C1 | incident optical axis |
| C2 | first axis |
| C3 | second axis |
| C5 | optical axis (fourth axis) |
| 1, 20 | endoscope optical system |
| 2 | cover glass (first optical member) |
| 3 | negative lens |
| 5 | first prism |
| 6, 21 | second prism |
| 6a | reflecting surface (first reflecting surface) |
| 7 | aperture stop |
| 8 | positive lens |

| {Reference Signs List} | |
|---|---|
| 16 | flat glass plate (second optical member) |
| 17 | image-acquisition surface |
| 21a | first reflecting surface |
| 21b | second reflecting surface |
| 22 | third prism |

The invention claimed is:

1. An endoscope optical system comprising a negative lens that focuses light entering along an incident optical axis, a first prism that deflects and emits the light that has been focused by the negative lens in a direction along a first axis substantially orthogonal to the incident optical axis, a second prism that has a first reflecting surface, which deflects the light emitted from the first prism in a direction of a second axis substantially orthogonal to the first axis, and a second reflecting surface that deflects and emits the light, which has been deflected in the direction of the second axis, in a returning direction substantially parallel to the first axis, and that is disposed so as to face the first prism, a third prism that deflects the light, which has been emitted from the second prism, in a direction substantially parallel to the incident optical axis, and a positive lens that focuses the light emitted from the third prism, in this order from an object side, wherein the negative lens and the first prism are provided so as to be rotatable about the first axis relative to the second prism, and wherein refractive indices of the first prism, the second prism, and the third prism satisfy the following conditional expression $$1.7 < (Np1+Np2+Np3)/3 < 2.4 \qquad (3)$$

where Np1 is a d-line refractive index of the first prism, Np2 is a d-line refractive index of the second prism, and Np3 is a d-line refractive index of the third prism.

2. An endoscope optical system according to claim 1, wherein the incident optical axis and the optical axis of the positive lens are disposed in substantially the same plane.

3. An endoscope optical system according to claim 1, wherein a length along the optical axis in the first prism, a length along the optical axis in the second prism, and a length along the optical axis in the third prism satisfy the following conditional expressions $$0.8 < DP1/DP2 < 1.2 \qquad (2)$$

$$0.8 < DP1/DP3 < 1.2 \qquad (4)$$

where DP1 is a length along the optical axis in the first prism, DP2 is a length along the optical axis in the second prism, and DP3 is a length along the optical axis in the third prism.

4. An endoscope optical system according to claim 1, wherein a length along the optical axis in the second prism and a length along the optical axis in the third prism satisfy the following conditional expression $$0.5 < DP2/DP3 < 7 \qquad (5)$$

where DP2 is a length along the optical axis in the second prism, and DP3 is a length along the optical axis in the third prism.

5. An endoscope optical system according to claim 1, further comprising an aperture stop that is disposed between the negative lens and the positive lens.

* * * * *